United States Patent [19]

Raible

[11] Patent Number: 5,501,574

[45] Date of Patent: * Mar. 26, 1996

[54] BLOOD PUMP

[75] Inventor: Donald A. Raible, Santa Ana, Calif.

[73] Assignee: Baxter International Inc., Deerfield, Ill.

[ * ] Notice: The portion of the term of this patent subsequent to Nov. 29, 2011, has been disclaimed.

[21] Appl. No.: 336,964

[22] Filed: Nov. 10, 1994

Related U.S. Application Data

[63] Continuation of Ser. No. 83,405, Jun. 28, 1993, Pat. No. 5,368,438.

[51] Int. Cl.$^6$ ...................................................... F04D 1/08
[52] U.S. Cl. ............................ 415/74; 415/143; 415/230; 415/900; 416/177
[58] Field of Search ................................. 415/71, 72, 73, 415/74, 143, 199.6, 230, 900; 416/176, 177

[56]  References Cited

U.S. PATENT DOCUMENTS

| | | | |
|---|---|---|---|
| 2,984,189 | 5/1961 | Jekat | 415/74 |
| 3,087,435 | 4/1963 | Boucher | 415/72 |
| 3,918,831 | 11/1975 | Grennan | 415/143 |
| 4,877,368 | 10/1989 | Timperi et al. | 415/72 |
| 5,040,944 | 8/1991 | Cook | 415/72 |
| 5,139,391 | 8/1992 | Carrouset | 416/177 |
| 5,368,438 | 11/1994 | Raible | 415/74 |
| 5,382,092 | 1/1995 | Okamoto et al. | 416/177 |

FOREIGN PATENT DOCUMENTS

| | | | |
|---|---|---|---|
| 317687 | 5/1989 | European Pat. Off. | 415/143 |
| 1118405 | 6/1956 | France | 415/230 |

Primary Examiner—Edward K. Look
Assistant Examiner—James A. Larson
Attorney, Agent, or Firm—Raymond Sun

[57]  ABSTRACT

A dynamic blood pump includes a rotating core member and rotating ring portion effective to pre-spin blood before the blood enteres helical pumping channels of the pump. The blood is pumped and further rotated as it moves axially along the helical channels toward a centrifugal section of the pump. At the centrifugal pumping section circumferential velocity differentials are also controlled to diminish damage to the blood. Outwardly of the centrifugal pumping section, a forced-vortex pumping section communicates the pumped blood to an exit port.

10 Claims, 3 Drawing Sheets

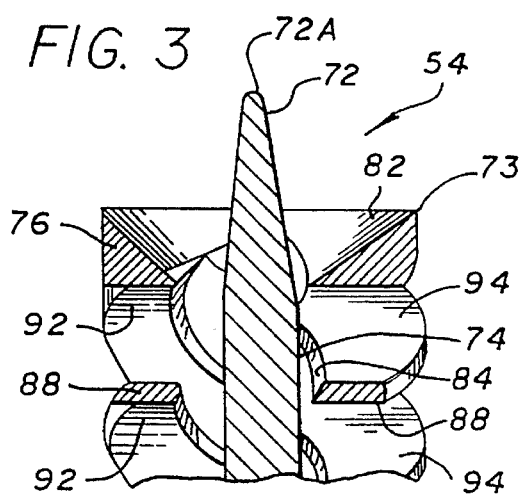
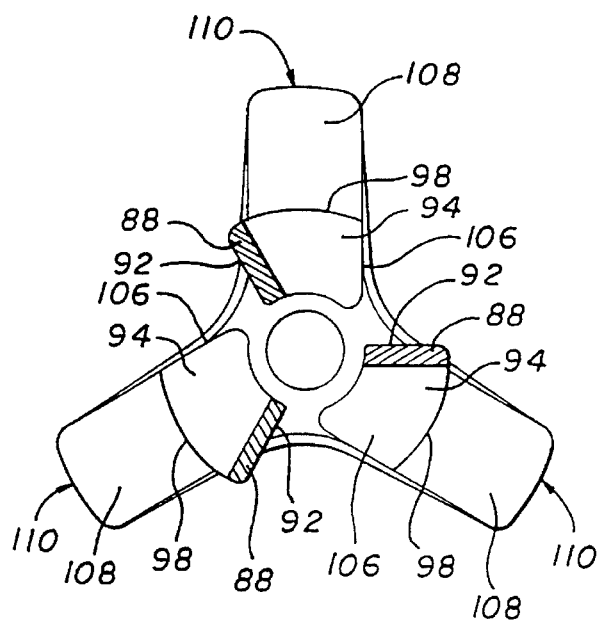
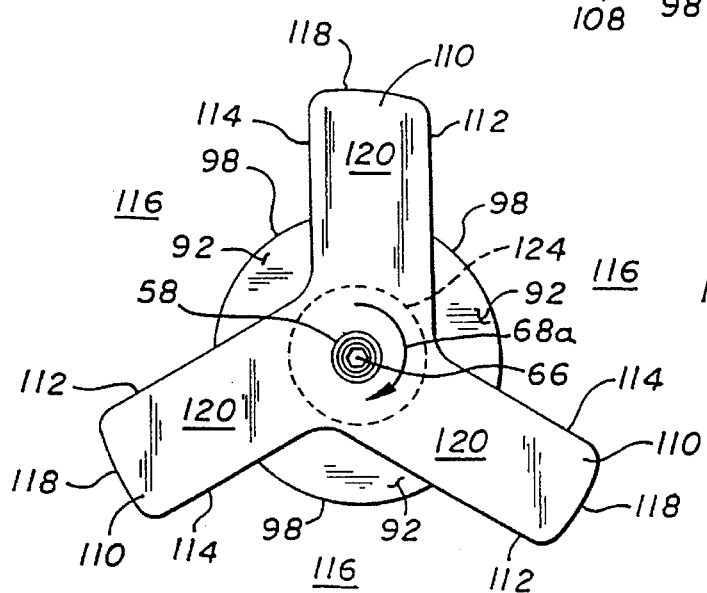
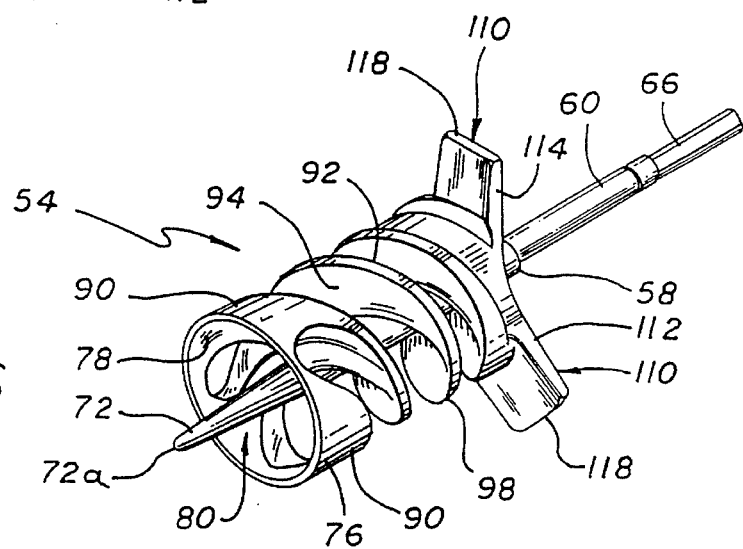
FIG. 3
FIG. 4
FIG. 5
FIG. 6

BLOOD PUMP

This is a continuation of U.S. patent application Ser. No. 08/083,405, filed Jun. 28, 1993, now U.S. Pat. No. 5,368,438.

BACKGROUND OF THE INVENTION

1. Field of the Invention

The present invention is in the field of liquid pumps. More particularly, the present invention is in the field of combined axial and centrifugal pumps for pumping liquids. Still more particularly, the present invention relates to a combined axial and centrifugal pump having a centrifugal-flow section and an axial-flow helical inducer section conveying liquid flow to the centrifugal section. The present inventive pump has particular utility for pumping blood with minimal damage to the formed cells and other constituents of the blood.

2. Related Technology

Blood is a complex and delicate fluid. Blood is essentially made up of plasma, which is a pale yellow liquid containing microscopic materials including the formed constituents of the blood. These formed constituents include the red corpuscles (erythrocytes), the white corpuscles (leukocytes), and the platelets (thrombocytes). These and other constituents of the blood, as well as the suspension of the formed constituents of the blood in the plasma, are affected by the manner in which blood is physically handled or treated. Moreover, blood is susceptible to damage from a variety of physical effects. These include depressurization, shock, shear, impact, other forms of physical stress, as well as turbulence, and sudden changes in cross sectional area of a flow path which causes eddy currents, and which may cause small clots to form in the blood.

Further to the above, it is well recognized that the conventional type of positive-displacement roller pump which has many uses in the medical field, and which employs a length of flexible tubing squeezed in progressive sections between a housing and moving rollers is hard on the formed constituents of the blood. These formed blood constituents become caught in the moving nips formed as the rollers move along and squeeze the flexible tubing. When so caught and squeezed, the formed constituent cells are ruptured and destroyed.

During many major surgical procedures, such as open heart surgery, or cardiovascular-respiratory support, the need to pump blood arises. This blood pumping necessity arises in connection with the requirement to move blood for the patient through heart-lung systems which filters the blood, removes impurities, oxygenates the blood, and controls its temperature to a level which reduces the patient's metabolism during the surgery. However, as pointed out above, pumping of blood is a particularly difficult problem. Such is the case because blood is not a simple liquid which can be pumped as though it were water or oil, for example. As explained above, blood contains many cells, such as red and white corpuscles, and other constituents which are living tissues of the body. These living blood tissues are particularly susceptible to damage and destruction by pumping actions which squeeze the blood, as do roller type pumps. Also, pumps which subject the blood to sudden changes in direction or velocity, which excessively stir the blood, which subject the blood to high relative velocities, or which submit the blood to excessive levels of shear, all impose damage on the blood, and impose a trauma on a living tissue of the patient undergoing the surgery or medical procedure.

Many attempts have been made to provide dynamic pumps which avoid the deficiencies of the conventional roller pump and other conventional pumps. One of these conventional blood pumps is known in accord with U.S. Pat. Re. 28,742, reissued 23 Mar. 1976, to E. H. Rafferty, et al. The Rafferty reissue patent is believed to teach a dynamic blood pump based on the forced vortex principle. That is, the pump is based on the principle that a spinning chamber forms therein a spinning volume of liquid which is pressurized at its outer periphery and flows radially outwardly. The Rafferty pump defines one or a successive plurality of such spinning chambers, the walls of which may be smooth with the exception of strut members or other such structural features arranged to connect the walls together for rotation in unison, or which may include radially extending and perhaps forwardly or backwardly inclined or swept vanes. In this context, the terms forwardly or backwardly inclined or swept vanes refer to the circumferential direction in which the vanes extend with respect to the normal direction of rotation of such a pump rotor. When so equipped with vanes extending into the pumping chambers from the rotating wall surfaces, the pump configurations of Rafferty are more akin to centrifugal pumps than to strict forced vortex pumps, the latter which rely on viscous coupling between the rotating walls of the pump and the liquid to effect spinning and pressurization of the latter.

As may easily be appreciated, the struts and other structural features of the pumps of Rafferty, and particularly the vanes of these pumps which are of centrifugal configuration may impose severe damage on formed blood cells. That is, the struts are spaced outwardly from the axis of rotation and sweep through the blood with a high relative circumferential velocity. Similarly, the vanes of the centrifugal versions of Rafferty's pumps have edges which may result in abrupt changes in cross sectional area of the blood flow channels, in turbulence and in shock to the formed constituents of the blood.

Another series of dynamic pumps which are based on the forced vortex principle and viscous coupling of the blood with the pumping rotors are seen in U.S. Pat. Nos. 3,864,055; 3,647,324; 3,970,408; 3,957,389; and 4,037,984. Considering particularly the first-listed one of these patents, it is seen that the pumping elements are based on forced vortex principles with the pumping chambers being of disk-like, semi-spherical, conical, or trumpet-shaped configurations. The pumping chambers include a pair of axially spaced apart rotating end wall members, and may include intermediate wall members which are matched in shape to the end wall members.

Experience has shown that with blood pumps made according to the teachings listed immediately above, the pumped blood experiences a higher than preferred level of damage. Also, some of these pump configurations are rather complex and expensive to manufacture. In the present medical environment with concerns about Hepatitis and AIDS mitigating toward a minimization of contact with a patient's blood, and the disposal of blood wetted equipment, the discarding of such pumping devices after a single use constitutes a significant expense.

Still additional conventional dynamic blood pumps are seen in U.S. Pat. Nos. 4,625,712, issued 2 Dec. 1986; and 4,846,152, issued 11 Jul. 1989, each having R. K. Wampler as a sole or coinventor. The blood pumps of the Wampler patents are small, high-speed, axial-flow designs of single or multiple stages, and the single stage design includes a slight increase in inner diameter of the flow path so that some centrifugal pumping effect is asserted.

The Wampler pumps have been found by experience to impose severe damage on the formed constituents of blood. It is believed that the high rotational speed which are required for the Wampler pumps to achieve significant volumes of pumped blood against ordinarily head pressures encountered in the use environments of such pumps is a significant factor in the great damage these pumps impose on the pumped blood.

Finally, another conventional blood pump of novel design is shown in U.S. Pat. No. 5,040,944, issued 20 Aug. 1991, to E. P. Cook. The Cook teaching includes a pump with an elongate central ribbon-like member which is helical and stationary. Around this central member rotates an elongate helical rod-like member which has a direction of helix opposite to the central member and which also rotates in this direction.

While the blood pump according to the Cook patent is believed to offer advantages in pumping volume and developed head pressure in comparison to other conventional blood pumps, the rotational speed required of this pump is still much higher than desired. Consequently, the Cook pump also imposes somewhat more damage on the pumped blood than that which is considered minimal and acceptable.

SUMMARY OF THE INVENTION

In view of the above, a primary object for the present invention is to provide a blood pump which results in significantly reduced damage to pumped blood.

Yet another object for the present invention is to provide such a blood pump which is economical to manufacture.

Another object for the present invention is to provide such a blood pump which avoids bluff or sharp-edged moving through the blood at excessive relative velocities.

Additional objects for the present invention are to provide a blood pump which is dependable, reliable, durable, and fully effective to accomplish its intended purposes of pumping blood with significant head pressures and volume flow rates without the level of damage to the blood which conventional blood pumps would cause.

Accordingly, the present invention provides a liquid pump with a housing defining an inlet, an outlet, and a flow path extending between the inlet and outlet for communicating a flow of liquid therebetween; a rotor member journaled in the flow path for impelling said liquid flow in response to rotation of said rotor member; the rotor member including a circumferentially continuous ring portion defining an inlet end for said rotor member and defining an inlet recess receiving therein said liquid flow from said inlet; a helical auger pumping section including plural helical flutes extending from said ring portion and cooperatively defining a like number of helical pumping channels open radially outwardly toward a circumferential wall portion of said housing and extending axially and circumferentially toward said outlet; said helical channels opening radially, axially, and circumferentially from said inlet recess; and a centrifugal pumping section including plural vane portions like in number to said helical flutes and each extending radially outwardly into a circumferential chamber of said flow path to cooperatively define circumferentially extending chamber sectors therebetween, each of said helical auger flutes merging with a respective one of said vane portions, and each of said helical pumping channels communicating with a respective one of said chamber sectors.

An advantage of the present inventive pump is that it avoids sudden changes in cross sectional area of the developed fluid flow area through the pump. Consequently, sudden changes in fluid flow velocity, turbulence, and impacts to the fluid, are also avoided. Also, the present inventive pump does not require the high rotational speeds of some conventional blood pumps in order to pump significant quantities of blood against the head pressures commonly encountered in such uses of the pump. As a result, the present inventive blood pump does not whip the blood like some of the conventional blood pumps.

As will be further elaborated hereinafter, actual comparative tests of several conventional blood pumps, and of blood pumps made according to the teaching of the present invention, have shown significant advantage for the present pump. That is, the rotational speeds required for the present pump are significantly lower. The damage imposed on the pumped blood per unit of time at a given pumping volume and head pressure, or per unit of blood pumped, is significantly lower for the present inventive blood pump than for the best of the conventional blood pumps discussed above. When it is remembered that the formed constituents of blood are living tissues of the patient, and that damage and destruction of these tissues results in necrotic factors which must be eliminated from the patient's system by the liver and kidneys for the most part, the burden on the patient's system from this cell damage must be minimized. In addition to slowing the patient's recovery, the damaged blood cells must eventually be replaced by the patient's system, which is another factor in patient recovery. These recovery-slowing burdens and trauma to the patient can be minimized by the use of the present inventive blood pump.

These and additional objects and advantages of the present inventive pump will be apparent from a reading of the following description of a particularly preferred exemplary embodiment of the present invention, taken in conjunction with the following drawing Figures, in which:

DESCRIPTION OF THE DRAWING FIGURES

FIG. 1 provides a fragmentary elevation view, partially in cross section, and somewhat schematically presented, of a pump embodying the present invention;

FIG. 3 is a fragmentary cross sectional view taken at line 3—3 of FIG. 1;

FIG. 4 is a cross sectional view taken at line 4—4 of FIG. 1;

FIG. 5 is a cross sectional view taken at line 5—5 of FIG. 1;

Figure 1:
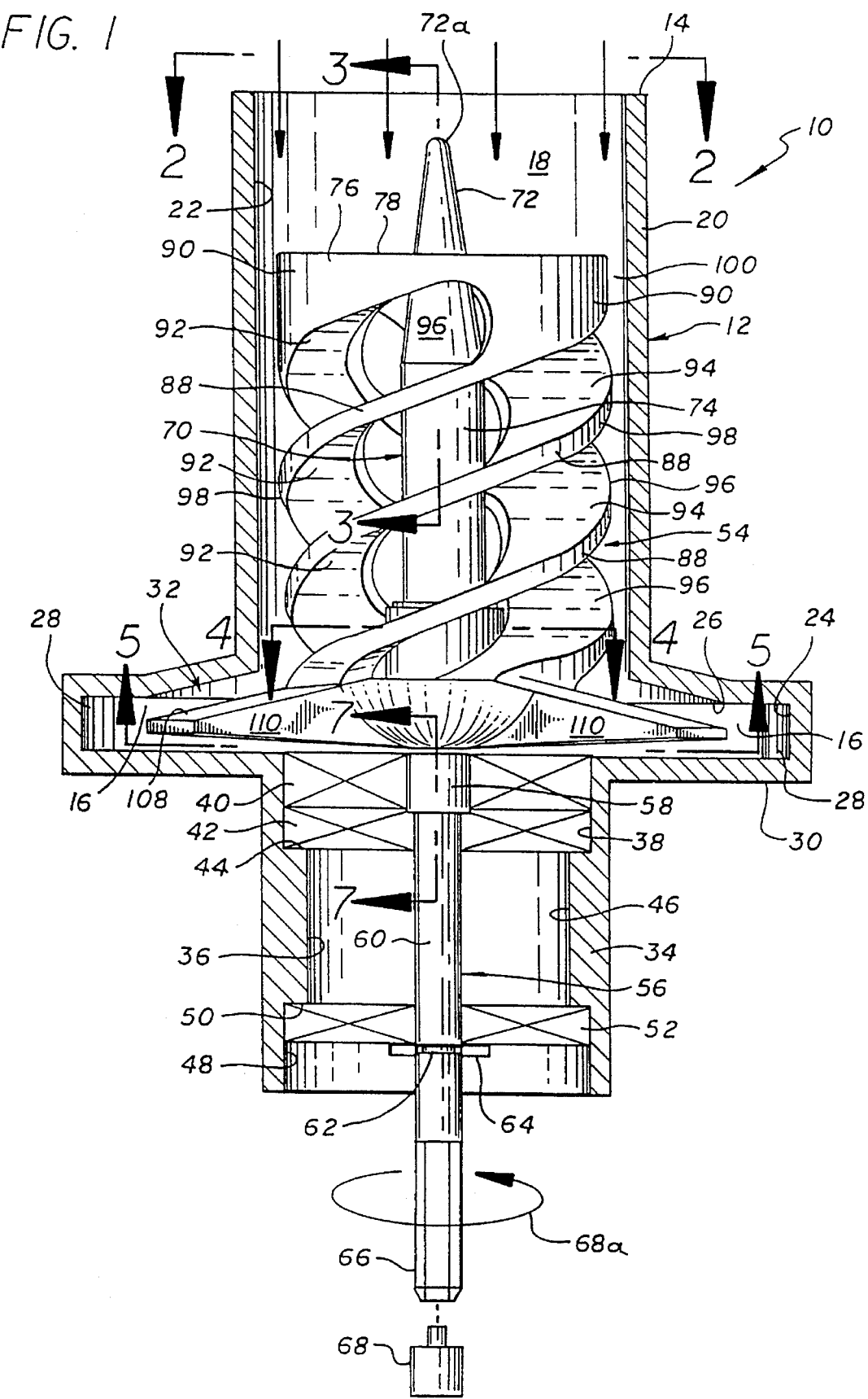
Figure 8:
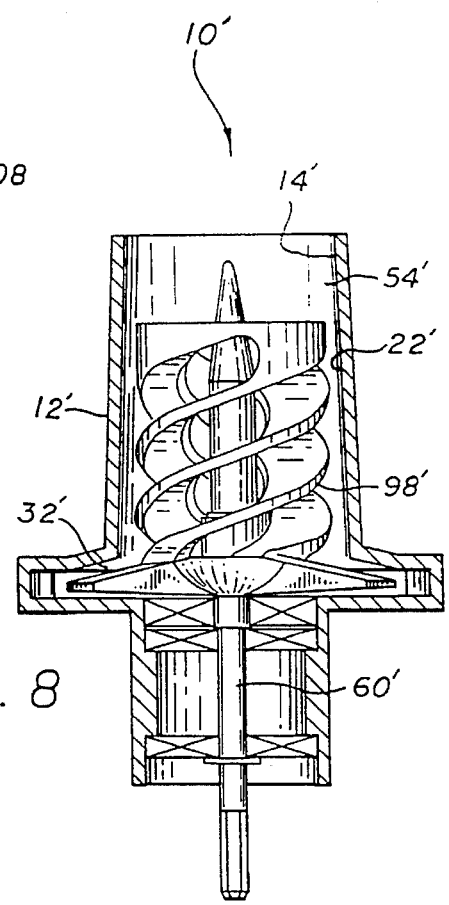
Figure 7:
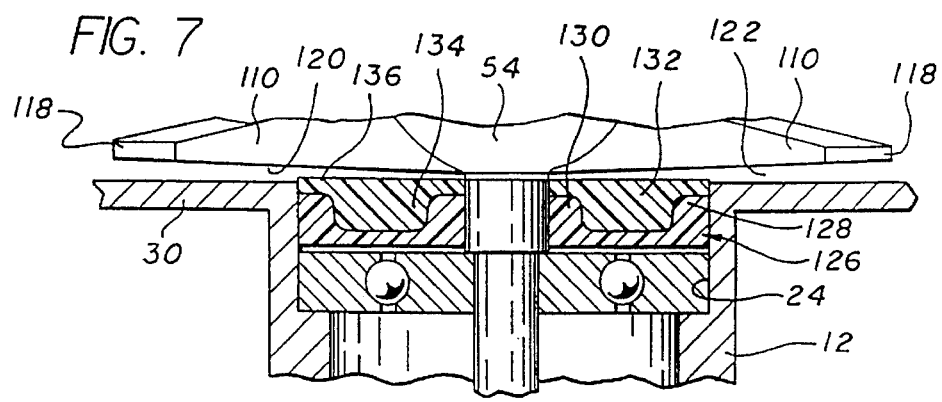

FIG. 6 presents an isolated perspective view of a component part of the inventive pump depicted in FIG. 1;

FIG. 7 is an enlarged fragmentary cross sectional view taken at line 7—7 of FIG. 1; and FIG. 8 is a fragmentary elevation view partially in cross section like FIG. 1, but showing an alternative embodiment of the present inventive pump.

DESCRIPTION OF THE PREFERRED EXEMPLARY EMBODIMENTS

Viewing FIGS. 1–6 in conjunction, it is seen that a pump 10 includes a housing 12. The housing 12 includes an inlet port, generally referenced with the numeral 14, plural outlet ports, each referenced with the numeral 16, and a flow path 18 communicating the inlet port 14 with the outlet ports 16. More particularly, the housing 12 includes a wall portion 20 which is circumferentially and axially extending to define a cylindrical bore 22. The cylindrical bore 22 at its upper end defines inlet port 14, and communicated downwardly to a larger diameter bore portion 24. Cooperatively, the bore portions 22 and 24 define a somewhat tapered shallow conical shoulder 26 on the housing 12. A circumferential wall portion 28 of the housing 12 cooperates with the shoulder 26 and with a planar back wall portion 30 to define a circumferential chamber 32 in the flow path 18. The wall portion 28 defines plural outlet ports 16 opening circumferentially outwardly from the chamber 32.

Below the back wall 30, the housing 12 includes a boss 34 which defines therein a stepped bore 36. In this stepped bore 36 at an upper larger diameter portion 38 thereof are received a sealing member 40 and a next adjacent upper bearing member 42. The bearing member 42 rests upon an upwardly disposed shoulder 44 formed on the bore 36 by cooperation of the portion 38 thereof with a smaller diameter bore portion 46. This smaller diameter bore portion 46 also cooperates with a lower larger diameter portion 48 of the bore 36 to define a downwardly disposed shoulder 50. In the bore portion 48, a second bearing member 52 is disposed in engagement with the shoulder 50.

As is seen in FIGS. 1 and 6, a rotor member, generally referenced with the numeral 54 is rotatably journaled in the flow path 18. The rotor member 54 includes an elongate shaft portion 56 having an upper seal runner 58 disposed in the sealing member 40, and a smaller diameter stem portion 60 rotationally supported by the bearing members 42 and 52. The seal runner portion 58 bears on the upper bearing member 42. Below the bearing 52, the stem portion 60 of shaft 56 includes a circumferential groove 62 in which is received a retaining ring 64. The retaining ring 64 bears on bearing 52 to capture the sealing member 40, bearings 42 and 52, and shaft 56 in the boss 34. Consequently, the rotor member 54 is rotatably journaled and axially constrained in the flow path 18. In order to rotationally drive the rotor member 54, a lower drive portion 66 is hexagonal in cross section to drivingly engage with a driving motor 68, which is schematically depicted. Rotation of the rotor member 54, when viewed from the stem end 66 is clockwise, as is indicated by arrow 68a.

Viewing FIGS. 1–6 in conjunction with one another, it is seen that the rotor member 54 includes an elongate central core member 70, which includes a conical portion 72 having a tip 72a confronting the inlet port 14, and leading to an elongate cylindrical portion 74. Circumscribing the core member 70 at the conical portion 72 thereof is a circumferentially continuous ring portion 76. This ring portion 76 defines an axial entrance end 78 for the rotor member 54, and also defines an opening into a conical and annular entrance recess 80. The conical entrance recess 80 includes conical surface portions 82, which are best seen viewing FIGS. 2, 3, and 6. It will be noted that in FIG. 2, the wall portion 20 and shoulder 26 are omitted to provide a better view of the rotor member 54 in the chamber 32. The inner diameter 84 of the conical entrance recess 80 is slightly larger in diameter than the cylindrical portion 74 of core member 70, and is about coextensive with the upper end of this conical core portion, to define a radial clearance 86. As is seen in FIGS. 1, 3, and 6, the conical portion 72 of the core member 70 extends out of the recess 80 toward the inlet port 14 so that upon liquid flow approaching the rotor member 54, the cross sectional flow area of flow path is first gradually decreased by the conical portion 72 of the core member 70, and then is additionally gradually reduced as the liquid flow enters into the conical entrance recess 80.

Extending axially and circumferentially from the ring portion 76, the rotor member 54 includes three helical flute portions 88. As is best seen in FIGS. 1 and 6, the ring portion 76 includes transition sections 90 connecting the circumferentially extending body of the ring member 76 with the axially angulated helical flutes 88, and the flutes 88 are equally spaced apart circumferentially. Each flute portion 88 includes a radially extending pressure surface 92 disposed toward the chamber 32, and an axially opposite radially extending suction surface 94 which is disposed toward the inlet 14. Circumferentially successive ones of the flutes 88 cooperate with one another at their surfaces 92 and 94 to define a like plurality of radially extending helical channels 96, which open radially outwardly toward the housing wall portion 20. An outer circumferential and helical surface 98 is spaced from the wall portion 20 to define a radial gap 100. Preferably, the gap 100 is in the range from about 0.025 to about 0.040 inches (about 0.6 to about 1.3 mm).

Figure 2:
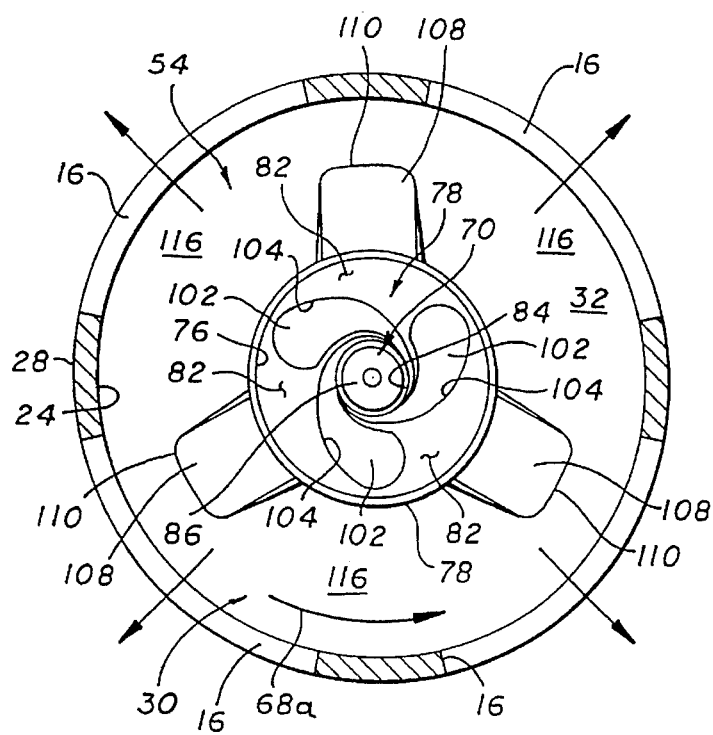
FIG. 2 is a fragmentary cross sectional view taken along line 2—2 of FIG. 1, and with parts of the structure omitted to better depict salient features of the invention.

Viewing FIGS. 2 and 6, it is seen that each of the channels 96 opens radially outwardly, axially, and circumferentially from the entrance recess 80. Consequently, when viewed in axial view as is seen in FIG. 2, the channels 96 each define what appears to be a tear drop shaped entrance opening 102 opening outwardly from the entrance recess 80 into the helical channels 96. Still considering the axial view of FIG. 2, it is seen that what appears as a floor of these entrance openings 102 is the suction surface 94 of the next preceding flute in the direction of rotation. Also, a circumferentially extending and helical leading edge 104 for the pressure surface 92 of the respective flute 88 is spaced axially toward the viewer of FIG. 2 with respect to the viewed portion of surface 94.

FIGS. 1 and 6 illustrate that the flutes 88 each proceed through slightly more than one complete turn around the core 70 and then define a termination end 106 on an axially disposed surface 108 on a respective one of plural centrifugal vanes 110. That is, the number of vanes 110 is equal to the number of flutes 88. Viewing FIGS. 2, 4, and 5, it is seen that the vanes 110 are generally radially extending, but are offset slightly in the circumferential direction of rotation to define a larger radially and axially extending pusher surface 112, and a smaller follower surface 114. In other words, viewing FIG. 5 more particularly, it is seen that the vanes 110 are of generally constant width, extend generally radially, and are circumferentially offset in the direction of rotation with respect to the rotational axis of the rotor member 54 which is defined at the stem 60. As a result, the pusher surfaces 112 would be tangent to a larger circle about the rotational axis at stem 60 than would the follower surfaces 114. This result of the circumferential offset of the vanes 110 can easily be seen by reference to the dash circle 124 of FIG. 5 because the pusher surfaces 112 are outside of this circle, and would not intersect with it if projected inwardly. In contrast, an inward projection of the follower surfaces 114 would intersect with the dash circle 124. Considering FIGS. 1 and 6 again, it is to be noted that each of the channels 96 opens smoothly into a respective circumferentially extending sector of the chamber 32 between the vanes 110, which chamber sectors are referenced with the numeral 116.

Viewing FIGS. 1, 6, and 7, it is seen that the vanes 110 have rounded surfaces, and define an outer end 118 which is spaced radially from the circumferential wall 28. Additionally, these vanes taper radially outwardly as they extend into the circumferential chamber 32. FIGS. 1 and 7 depict that the vanes 110 are also tapering axially toward the inlet 14 on their back surfaces 120. That is, the vanes 110 cooperate with the generally planar back wall 30 of the chamber 32 to define an axially extending and radially outwardly increasing gap 122. It will be noted that between the vanes 110, the gap 122 virtually does not exist because the chamber sectors 116 extend radially inwardly close to the seal runner 58. However, viewing FIG. 5, it is seen that around the seal runner 58 there is a circle denoted with dashed line 124, within which the gap 122 is circumferentially complete.

FIG. 7 shows that at the seal runner 58, the sealing member 40 includes a resilient polymeric cup seal 126, having a radially outer lip 128 which sealingly engages the housing 12 at bore portion 24. This cup seal 126 also includes a radially inner lip 130 which forms a dynamic seal with the rotational seal runner portion 58 of shaft 56. Between the lips 128 and 130, the cup seal 126 defines a circumferentially extending axial groove 132. Disposed in the groove 132 is a low-friction blood compatible polymeric filler member 134, which defines a planar upper surface 136 disposed toward and in closely spaced relation with the back surface 120 of rotor member 54. Importantly, within the circle 124 (recalling FIG. 5), the filler member 134 substantially fills the gap 122.

Having observed the structure of the pump 10, attention may now be turned to its operation. With the flow path 18 filled with liquid (the pump 10 not being self-priming) rotation of the rotor member 54 by drive motor 68 as indicated by arrow 68a, impels liquid flow along the flow path 18 toward the entrance end 78 of rotor 54. As this liquid flow approaches the rotor member 54 it first encounters the conical end portion 72 of core member 70. Shortly thereafter, the liquid flow encounters the entrance end 78 of ring portion 76 leading to entrance recess 80, and flows therein. Considering the experience of the liquid to this point, is seen that abrupt changes in cross sectional area developed in the flow path 18 by the cooperation of housing 12 and rotor member 54 are avoided. Additionally, the ring portion 76 and core 70 with its conical end portion 72 extending axially into the approaching liquid flow are spinning. Consequently, a pre-spin is provided to the approaching liquid by viscous coupling therewith.

Once this pre-spun liquid is in the entrance recess 80, it encounters the circumferentially swept leading edges 104 of the entrance openings 102 into the helical channels 96. These leading edges 104 are rounded so as not to impose impacts on the formed constituents of blood pumped with the pump 10. Further, the leading edges 104 lead radially outwardly and helically to the channels 96. Consequently, the spinning liquid in entrance recess 80 has a tendency to move by its own centrifugal force into the helical channels 96.

Once in the helical channels 96, the liquid is subjected to a greater level of viscous coupling with spinning rotor member 54, so that the liquid has a tendency to spin more and more with the rotor member as it moves along channels 96. However, the channels 96 open radially outwardly toward and are bounded generally by the outer wall 20. Consequently, the viscous drag provided by the outer wall 20 keeps the liquid from merely spinning with the rotor 54, and causes the liquid to advance along the channels 96. Importantly, the outer wall 20 is spaced from the outer circumferential surface 98 to define the radial gap 100. This gap is sized to be sufficiently small that back flow leakage is not excessive and does not result in excessive churning of the pumped liquid (recognizing that pumping inefficiency appears as work dissipated in the pumped liquid which does not appear as pressure or flow energy, and resulting in damage to formed blood constituents). On the other hand, the gap 100 is chosen to be sufficiently large that formed blood constituents which do pass through this gap with the back flow liquid are not subjected to excessive levels of shear. Recalling the explanation above of how conventional pumps damage and destroy the formed constituents of blood, it is easily appreciated that the size of gap 100 is best determined experimentally for each size and operating speed of pump 10. However, the liquid in the channels 96 does accelerate circumferentially as it moves along the channels 96 so that its circumferential velocity approaches that of the adjacent surfaces of the rotor member 54, as will be further explained.

As the channels 96 open into the chamber sectors 116, the respective pressure surface 92 leads to and blends into the pusher surface 112 of the chamber sector 116. Similarly, the suction surface of the channel 96 leads to and ends on the axial surface 108 of a respective vane 110 immediately adjacent to the respective follower surface 114. Consequently, at the transitions from the helical auger pumping section which is represented by the helical flutes 88 and the centrifugal pumping section which is comprised of vanes 110, the liquid flow is not subjected to any turbulence or pressure shock. Additionally, as noted above, the liquid has been circumferentially accelerating along the channels 96 so that by the time the liquid is discharged from these channels into the chamber 32 its circumferential velocity is nearly that of the adjacent surfaces of the rotor 54, and no subjecting of the liquid to surfaces moving through it at high relative velocity is experienced.

In the chamber 32, the liquid is radially and circumferentially accelerated by action of the vanes 110. The fact that these vanes have pusher surfaces 112 which are enlarged by the circumferential offset of the vanes relative to the shaft 56 is considered an important feature in the interest of minimizing damage to the formed constituents of blood pumped with the pump 10. Importantly, the vanes 110 terminate at radially outer ends 118 spaced radially from the circumferential wall 28 so that the pump 10 includes an element of forced vortex pumping in the chamber 32 outwardly of the vanes 110. From the chamber 32, the pumped liquid exits via plural radially extending outlet ports 16.

Recalling also FIG. 7, it will be seen that the filler member 134 performs two beneficial functions in the use environment of the pump 10. First, this filler member 134 fills the circumferential void created in the cup sealing member 126 between the lips 128 and 130. Consequently, the creation of a substantially stagnant void volume in this seal member is avoided. Those ordinarily skilled in the pertinent arts will recognize that such a stagnant void volume could cause blood clots to form, possibly to subsequently be sloughed off and to cause embolisms for the patient. Secondly, it must be recognized that the area between the back wall 30 and the back surfaces 120 of the rotor member 54 in gap 122 is an area of very high potential shear. This shear is aggravated as the space between relatively moving surfaces is decreased. Accordingly, adequate spacing is utilized, and the filler member 134 prevents blood from entering the area of high shear where the formed constituents of the blood would be damaged or destroyed.

FIG. 8 illustrates an alternative embodiment of the present inventive pump, which is the same in all respects except one, to the pump depicted and described by reference to FIGS. 1–7. In order to obtain reference numerals for use on FIG.

8, features which are analogous in structure or function to those depicted and described above are referenced on FIG. 8 using the same numeral used above, and having a prime added thereto. Viewing FIG. 8, it is seen that the pump 10' includes a housing 12' journaling a rotor member 54'. In contrast to the embodiments of FIGS. 1–7 however, the bore 22' is not truly cylindrical. This bore 22' is slightly tapered to enlarge from the inlet port 14' toward the chamber 32'. The housing 12' is made of a sterilizable injection molded polymer material, such as polycarbonate. Consequently, the bore 22' must be slightly tapered to allow withdrawal of a injection molding core therefrom. In fact, FIG. 8 illustrates the taper of bore 22' as being greater than that which may be required. However, this drawing Figure also illustrates that the rotor member 54' is similarly tapered so that the outer helical surfaces 98' taper to match the bore 22'.

The applicant has built and tested several sizes of pumps according to the present invention. Particularly, pumps of three different sizes having respective inlet conduit sizes of one-forth, three-eights, and one-half inch were tested. These pumps had sizes for the rotor member 54 measured at the outer diameter 98 of flutes 88 of three-forth, one, and one and three-sixteenths inches. At rotational speeds in the range of from 3500 to about 6000 rotations per minute, these pumps moved blood at respective volumes of 2, 4, and 7 liter per minute. Also, these specified blood movement volumes were achieved at respective head pressures of 150, 300, and 500 mm of mercury. In each case, the centrifugal pumping section of the pumps was the same three-armed member, of approximately one and three-quarters inches diameter. Very importantly, each of these actual embodiments of the present invention achieved the above specified pumping effect with human blood while realizing about a ten percent improvement (reduction) in the damage to formed cells of the blood in comparison to the best commercially available conventional dynamic blood pump.

While the present invention has been depicted, described, and is defined by reference to particularly preferred embodiments of the invention, such reference does not imply a limitation on the invention, and no such limitation is to be inferred. The invention is capable of considerable modification, alteration, and equivalents in form and function, as will occur to those ordinarily skilled in the pertinent arts. For example, instead of the mechanical drive from motor 68 to rotor 54 which is depicted in FIG. 1, this drive can be effected with a magnetic coupling, preferably of the hermetic type. Alternatively, a flex shaft can be used to transfer driving power to the rotor 54. The depicted and described preferred embodiments of the invention are exemplary only, and are not exhaustive of the scope of the invention. Consequently, the invention is intended to be limited only by the spirit and scope of the appended claims, giving full cognizance to equivalents in all respects.

I claim:

1. A liquid pump comprising:
   a housing defining an inlet, an outlet, and a flow path extending between the inlet and outlet for communicating a flow of liquid through said housing;
   a rotor member journaled in said flow path, said rotor member impelling said flow of liquid in response to rotation of said rotor member, said rotor member including:
   (a) plural helical fluid transport flutes defining an entrance recess and each helical flute extending axially from said entrance recess, said helical flutes cooperatively defining a like plurality of helical pumping channels opening radially outwardly and helically from said entrance recess;
   (b) an axially extending bore defined by said helical flutes within said rotor member, said bore having a central axis;
   (c) a core member rotating with said rotor member being received into and extending through said bore of said rotor member along the central axis of said bore, said core member being separate from said helical flutes; and
   (d) wherein the liquid flows from said entrance recess axially down said helical flutes to said outlet.

2. The liquid pump of claim 1 further including said helical flutes defining an outer diameter, said housing including a wall portion defining a housing bore which forms part of said flow path, said helical flutes being received in said housing bore to define a radial gap at said outer diameter with said wall portion.

3. The liquid pump of claim 2 wherein said outer diameter gap is in the range of from about 0.025 inch to about 0.040 inch.

4. The liquid pump of claim 2 wherein said helical pumping channels are open radially toward said housing wall portion.

5. The liquid pump of claim 1 further including a shaft portion of said rotor member being journaled by said housing, said housing comprising a seal member sealingly cooperating with said shaft portion to prevent escape of liquid from said flow path along said shaft portion, and said seal member including a pair of radially spaced apart lips axially disposed toward said flow path and cooperatively defining therebetween a circumferential recess opening toward said flow path and circumscribing said shaft portion, and a circumferential filler member disposed in said recess.

6. The liquid pump of claim 1, wherein said core member further comprises an upper end, and a conical tip provided at the upper end of said core member.

7. A liquid pump comprising:
   a housing defining an inlet, an outlet, and a flow path extending between the inlet and outlet for communicating a flow of liquid through said housing;
   a rotor member journaled in said flow path, said rotor member impelling said flow of liquid in response to rotation of said rotor member, said rotor member including:
   (a) plural helical fluid transport flutes defining an entrance recess and each helical flute extending axially from said entrance recess, said helical flutes cooperatively defining a like plurality of helical pumping channels opening radially outwardly and helically from said entrance recess;
   (b) an axially extending bore defined by said helical flutes within said rotor member;
   (c) a core member rotating with said rotor member being received into and extending through said bore of said rotor member; and
   (d) wherein the liquid flows from said entrance recess axially down said helical flutes to said outlet;
   wherein said rotor member further includes a like plurality of radially extending vane portions extending radially outward of said helical flutes.

8. The liquid pump of claim 7 wherein said vane portions are disposed axially at an opposite end of said helical flutes with respect to said entrance recess.

9. A method of pumping liquid in a flow path in response to rotation of a pump rotor journaled in said flow path, said method including the steps of:
   (a) providing a rotor member comprising:
      (i) a plurality of helical flutes, said helical flutes having an upper portion defining an entrance recess, said helical flutes extending axially from said entrance recess and cooperatively defining a plurality of helical pumping channels opening radially outward and helically from said entrance recess, (ii) an axially extending bore defined by said helical flutes within said rotor member, said bore having a central axis and (iii) a core member received into and extending through said bore of said rotor member along the central axis of said bore, said core member being separate from said helical flutes;

(b) using viscous coupling between said entrance recess and said liquid to pre-spin the latter as it approaches said entrance recess and before entry of said liquid into said helical pumping channels; and (c) flowing the liquid axially down said helical flutes.

10. The method of claim 9 further including the step of moving said liquid axially along said helical pumping channels while accelerating said liquid circumferentially toward the rotational speed of said rotor member.

* * * * *